United States Patent
Weder et al.

(10) Patent No.: US 10,323,129 B2
(45) Date of Patent: Jun. 18, 2019

(54) STIMULUS-RESPONSIVE SUPRAMOLECULAR GLASSES

(71) Applicant: ADOLPHE MERKLE INSTITUTE, UNIVERSITY OF FRIBOURG, Fribourg (CH)

(72) Inventors: Christoph Weder, Düdingen (CH); Diederik Balkenende, Giffers (CH); Gina Fiore, Marly (CH)

(73) Assignee: ADOLPHE MERKLE INSTITUTE, UNIVERSITY OF FRIBOURG, Fribourg (CH)

( * ) Notice: Subject to any disclaimer, the term of this patent is extended or adjusted under 35 U.S.C. 154(b) by 238 days.

(21) Appl. No.: 15/368,013

(22) Filed: Dec. 2, 2016

(65) Prior Publication Data
US 2017/0081480 A1    Mar. 23, 2017

Related U.S. Application Data

(63) Continuation-in-part of application No. PCT/EP2015/062270, filed on Jun. 2, 2015.

(60) Provisional application No. 62/007,088, filed on Jun. 3, 2014.

(51) Int. Cl.
  *C08G 83/00* (2006.01)
  *C08J 3/28* (2006.01)
  *C07D 403/14* (2006.01)
  *C07D 239/48* (2006.01)

(52) U.S. Cl.
CPC ......... *C08G 83/008* (2013.01); *C07D 239/48* (2013.01); *C07D 403/14* (2013.01); *C08J 3/28* (2013.01); *C08J 2375/04* (2013.01)

(58) Field of Classification Search
None
See application file for complete search history.

(56) References Cited

U.S. PATENT DOCUMENTS 6,683,151 B1 * 1/2004 Loontjens .......... C08G 18/3851
  106/18.32

FOREIGN PATENT DOCUMENTS

WO        0107396 A1    2/2001
WO    WO-2014185779 A1 * 11/2014 .......... C08L 101/005

OTHER PUBLICATIONS

Hirschberg, J.H., et al., Supramolecular Polymers from Linear Telechelic Siloxanes with Quadruple-Hydrogen-Bonded Units, Macromolecules, Mar. 10, 1999, vol. 32, pp. 2696-2705, published on Web.
Heinzmann, C., et al., Light-Induced Bonding and Debonding with Supramolecular Adhesives, ACS Applied Materials & Interfaces, Jan. 31, 2014, vol. 6, pp. 4713-4719.
Folmer, B.J., et al., Supramolecular Polymer Materials: Chain Extension of Telechelic Polymers Using a Reactive Hydrogen-Bonding Synthon, Advanced Materials, 2000, vol. 12, No. 12, pp. 874-878.
Buckle, H., Use of the Hardness Test to Determine Other Material Properties, The Science of Hardness Testing and Its Research Applications, Oct. 1971, Chapter 33, pp. 453-490.
Oliver, W.C., et al., Measurement of hardness and elastic modulus by instrumented indentaiton: Advances in understanding and refinements to methodology, Journal of Materials Research, Jan. 2004, vol. 19, No. 1, pp. 3-20.
Lange, R, et al., Hydrogen-Bonded Supramolecular Polymer Networks, Journal of Polymer Science, Part A, vol. 37, pp. 3657-3670, 1999, John Wiley & Sons, Inc.
Sijbesma, R.P., et al., Reversible Polymers Formed from Self-Complementary Monomers Using Quadruple Hydrogen Bonding, Science, vol. 278, 1997, pp. 1601-1604, AAAS, Washington, DC.
Sonntag, M., et al., Novel Star-Shaped Triphenylamine-Based Molecular Glasses and Their Use in OFETs, Chem. Mater., vol. 17, 2005, pp. 3031-3039, published on Web.
Cheng, C., et al., bioinspired hole-conducting polymers for application in organic light-emitting diodes, J. Mater. Chem., vol., 22, 2012, pp. 18127-18131.
Wang, Z., et al., Thermal-healable and shape memory metallosupramolecular poly(n-butyl acrylate co-methyl methacrylate) materials, RSC Adv., vol. 4, 2014, pp. 25486-25493.
Kuo, S, et al., Self-Complementary Multiple Hydrogen Bonding Interactions Increase the Glass Transition Temperatures to Supermolecular Poly(methyl methacrylate) Copolymers, Journal of Applied Polymer Science, vol. 123, 2012, pp. 3275-3282, Wiley Periodicals, Inc.

* cited by examiner

*Primary Examiner* — Christopher M Rodd
(74) *Attorney, Agent, or Firm* — Hudak, Shunk & Farine Co., L.P.A.

(57) ABSTRACT

Supramolecular polymers or materials that exhibit high stiffness and can efficiently be healed. The supramolecular materials polymer is based on monomers having three or more same or different binding sites that permit non-covalent, directional interactions between multiple monomer molecules. The properties of the supramolecular networks formed from the monomers are governed by cross-linked architecture and the large weight-fraction of the binding motif. The material in one embodiment forms a disordered glass, which in spite of the low-molecular weight of the building block, displays typical polymeric behavior. The material exhibits high stiffness and offers excellent coating and adhesive properties. On account of reversible dissociation and the formation of a low-viscosity liquid upon application of an optical stimulus or thermal stimulus or both, rapid healing as well as (de)bonding are possible.

17 Claims, 14 Drawing Sheets

STIMULUS-RESPONSIVE SUPRAMOLECULAR GLASSES

FIELD OF THE INVENTION

The present invention relates to supramolecular polymers or materials that exhibit high stiffness and can efficiently be healed. The supramolecular materials according to the present invention are based on monomers having three or more same or different binding sites that permit non-covalent, directional interactions between multiple monomer molecules. The properties of the supramolecular networks formed from the monomers are governed by their cross-linked architecture and the large weight-fraction of the binding motif. The materials of the present invention in one embodiment form a disordered glass, which in spite of the low-molecular weight of the building block, displays typical polymeric behavior. The materials exhibit high stiffness and offer excellent coating and adhesive properties. On account of reversible dissociation of the monomers and the formation of a low-viscosity liquid upon application of an optical stimulus or thermal stimulus or both, rapid healing as well as (de)bonding are possible.

BACKGROUND OF THE INVENTION

Supramolecular polymers are assembled from monomeric building blocks through non-covalent, directional interactions such as H-bonding, π-π stacking, and ligand-metal complexation. The nature and strength of useful supramolecular motifs can be varied over a wide range, and the reversible and in many cases dynamic nature of supramolecular binding can lead to stimuli-responsive properties. The possibility to temporarily reduce the molecular weight of the supramolecular assemblies by shifting the equilibrium to the monomer side by exposure to an appropriate stimulus (or alternatively to use systems that are highly dynamic at ambient and require no further activation) can be used to create healable (or self-healing) polymers, as the resulting increase of the chain mobility and decrease of the material's viscosity enable the disassembled material to flow and fill cracks and gaps, before the original material is reformed by shifting the equilibrium back to the assembled state. Examples of thermally healable materials based on this general concept include hydrogen-bonded rubbers based on telechelic poly-(ethylene-co-butylene) functionalized with 2-ureido-4[1H]-pyrimidinone (UPy) units, elastomer networks based on fatty acids, ethylene diamine, and urea, and phase-separated elastomers based on a polystyrene-polyacrylic acid brush copolymer. Optically healable supramolecular polymers, which are advantageous because the stimulus can be applied in a targeted manner, have also been realized, for example on the basis of telechelic poly(ethylene-co-butylene) that was chain-terminated with terdentate ligands and assembled into a polymer with stoichiometric amounts of $Zn^{2+}$ or $Eu^{3+}$. However, on account of the dynamic nature of the supramolecular motifs employed, and the use of building blocks with low glass transition temperature virtually all known healable supramolecular polymers exhibit a low resistance to mechanical stress. This problem can to a certain extent be overcome by the introduction of a rigid, reinforcing (nano)filler, but even with this improvement the stiffness (storage modulus of <250 MPa) and strength (tensile strength of <5 MPa) thus far reported are very limited, which represents an obstacle for the exploitation of such materials as a replacement of thermoset resins in coatings, adhesives, and other applications. While molecular glasses represent a well-investigated class of materials, polymeric supramolecular glasses have been rarely observed.

Accordingly, one problem of the present invention was to create supramolecular materials that exhibit relatively high stiffness and yet can efficiently be healed.

Still another problem of the present invention was to provide supramolecular materials that offer excellent coating and adhesive properties, and whose adhesive properties can be altered by an external stimulus such as light or heat to enable (de)bonding on demand.

SUMMARY OF THE INVENTION

The present invention provide supramolecular materials, e.g. polymers that solve the above-noted problems and others, wherein the supramolecular materials include at least one monomer, each monomer having three or more identical or different binding sites that provide non-covalent, directional interactions between multiple monomer molecules.

Still another object of the present invention is to provide supramolecular materials that exhibit relatively high stiffness in an un-switched state, wherein in one embodiment the materials are characterized by an elastic modulus of at least 500 MPa. In additional embodiments, the elastic modulus is at least 700 MPa, at least 900 MPa, or at least 2 GPa.

A further object of the present invention is to provide a supramolecular material that in an un-switched state is a material in a substantially disordered glassy state.

Yet another object of the present invention is to provide supramolecular materials that can be switched between a first, un-switched state and a second switched state that is inducible by an optical stimulus or a thermal stimulus or a combination thereof. In one embodiment the stimulus is light. In various embodiments, the material is heated through exposure to ultraviolet, visible, near infrared or infrared light or a combination thereof.

Another object of the present invention is to provide stimulus-responsive supramolecular material that utilizes only one monomer type having three or more identical or different binding sites that permit non-covalent, directional interactions between multiple monomer molecules. In yet a further embodiment, all of the binding sites are identical. In yet a further embodiment, the each monomer present has a molar mass of at least 1,000 g/mol.

Still another object of the present invention is to provide a method for healing a damaged portion of a stimulus-responsive supramolecular material present on an object or substrate, comprising the steps of heating the damaged portion to a temperature that is above a glass transition temperature of the material, for example at least 40° C. in one embodiment, for a suitable period of time, and subsequently cooling the material below the glass transition temperature.

Accordingly, in one aspect of the present invention, a stimulus-responsive supramolecular material is disclosed, comprising at least one monomer having three or more identical or different binding sites that permit non-covalent, directional interactions between multiple monomer molecules, wherein in a first un-switched state the material is in a substantially disordered glassy state and is characterized by an elastic modulus of at least 500 MPa, and wherein in a second switched state, the material is in a fluid state, wherein switching between the first un-switched state and the second switched state is inducible by an optical stimulus or thermal stimulus or a combination thereof.

A further aspect of the present invention provides a method for healing a damaged portion of a stimulus-responsive supramolecular material present on an object, wherein the material comprises at least one monomer having three or more identical or different binding sites that permit non-covalent, directional interactions between multiple monomer molecules, wherein in a first un-switched state the material is in a substantially disordered glassy state and is characterized by an elastic modulus of at least 500 MPa, and wherein in a second switched state, the material is in a fluid state, wherein the method comprises heating the damaged portion to a temperature that is above a glass transition temperature of the material for a period of time, and subsequently cooling the material to below the glass transition temperature.

BRIEF DESCRIPTION OF THE DRAWINGS

The invention will be better understood and other features and advantages will become apparent by reading the detailed description of the invention, taken together with the drawings, wherein.

DETAILED DESCRIPTION OF THE INVENTION

Figure 1A:
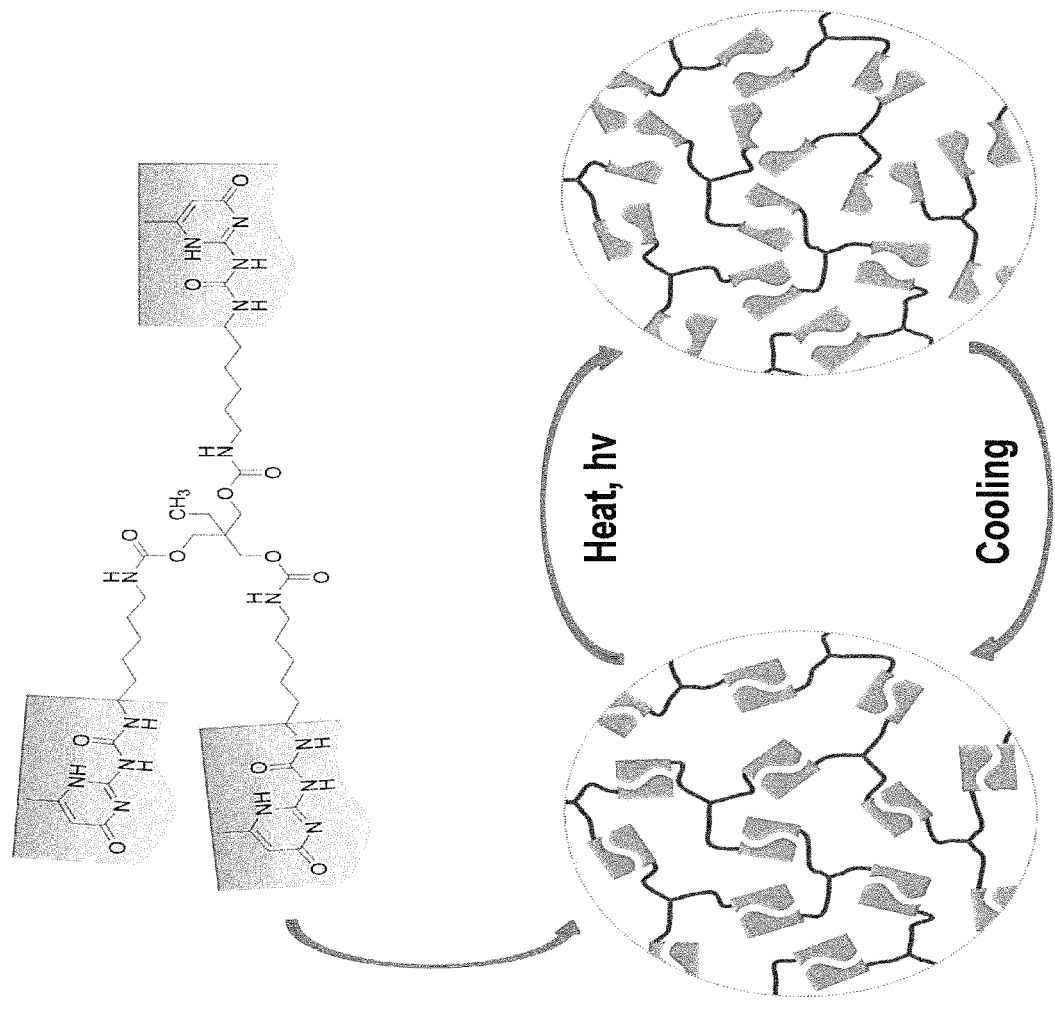
FIG. 1 illustrates supramolecular glasses based on (UPyU)$_3$TMP, including a) Schematic representation of the formation of disordered supramolecular networks based on (UPyU)$_3$TMP and their reversible, heat- or light-induced dissociation, b) Synthesis of (UPyU)$_3$TMP by the dibutyltin-dilaurate-catalyzed reaction of 1,1,1-tris(hydroxymethyl) propane (1) with three equivalents of 2-(6-isocyanatohexy-laminocarbonylamino)-6-methyl-4[1H]pyrimidinone (2) in hot DMF, and c) Picture of a self-supported (UPyU)$_3$TMP film prepared by compression molding at 140° C. and 3 tons of load for 1 minute. After cooling to room temperature, careful demolding resulted in a self-standing film.

The stimulus-responsive supramolecular materials of the present invention include at least one monomer, with each monomer having three or more identical or different binding sites that permit non-convalent, directional interactions between multiple monomer molecules. Examples of non-covalent binding motifs (those skilled in the art will readily be able to discern between self-complementary motifs, in which case all binding sites can be identical, or hetero-complimentary motifs, where at least two different binding sites must be used) include, but are not limited to, the following: motifs based on the UPy group, carboxylic acid dimers, carboxylic acid-amine pairs, nucleobase pairs, diaminopyridine-uracil, and other hydrogen-bonding motifs; metal-ligand complexes such as bipyridine or terpyridine transition metal complexes; charge-transfer complex such as based on pyrenyl and naphtimide groups. If motifs are employed that do not bind in a self-complementary manner, either multiple supramolecular monomers are used, or one supramolecular monomer with both groups is employed. The supramolecular monomers according to the present invention may carry two, three, or more binding motifs, but preferably more than two. While molecular glasses represent a well-investigated class of materials, supramolecular polymer glasses based on small molecules have been rarely observed and remain little explored. Known examples of such materials show either a glass transition close to room temperature or the tendency to crystallize above their glass transition temperature (Tg). The stimulus-responsive supramolecular materials according to the present invention exhibit a high Tg and a low tendency to crystallize upon cooling from the melt.

The stimulus-responsive supramolecular material in one embodiment is, in a first, unswitched state, a substantially disordered glass. In the un-switched state, the material has an elastic modulus generally of at least 500 MPa, desirably at least 700 MPa, preferably at least 900 MPa, and most preferably more than 2 GPa.

Switching between the first un-switched state and a second, switched state is inducible by one or more stimuli including, but not limited to, an optical stimulus and a thermal stimulus. In one embodiment, the stimulus is light, with the light being one or more of ultraviolet, visible, near infrared or infrared light. In various embodiments, in the first unswitched state, the material has a glass transition temperature of at least 40° C., and preferably more than 100° C.

The supramolecular material in the second, switched state is a fluid. Depending on the particular material, the viscosity can vary. In various embodiments, in the second switched state, the material is a Newtonian fluid. In other embodiments, in the second switched state, the material is a non-Newtonian fluid. In one embodiment, at up to 160° C. we have a non-Newtonian liquid, that means that there is a frequency dependence on the viscosity, and at 160° C. we observe Newtonian behavior from 160° C. and higher, wherein zero shear viscosities from 80° C. are 8.3*10ˆ6 Pa·s and at 150° C. are 4.0*10ˆ3 Pa·s.

The stimulus-responsive supramolecular material in one embodiment is formed from monomers consisting of only one monomer type, with each monomer having three or more identical or different binding sites that permit non-covalent, directional interactions between multiple monomer molecules. Accordingly, the particular monomers can form strong, self-complimentary hydrogen-bonded dimers. In one preferred embodiment, the binding sites are identical. Monomers comprising the ureido-4-pyrimidinone (UPy) groups are utilized. The monomers in various preferred embodiments have a molar mass of at least 1,000 g/mol.

Composites including a stimulus-responsive supramolecular material and another object such as a substrate are disclosed in the present invention. The supramolecular materials can be utilized as coatings on various substrates including, but no limited to, wood, glass, paper, or even other polymeric materials. According to the present invention, the supramolecular materials can also include a reinforcing filler, for example cellulose nanocrystals. According to one embodiment of the present invention, it is advantageous to equip the filler with binding sites that permit non-covalent, directional interactions with the monomer molecules.

The supramolecular materials of the present invention are self-healing and damage to a portion of the material can be repaired upon exposure to light or heat or a combination thereof. As discussed further herein, damage to a portion of the material can be healed or removed by heating the damaged portion to a temperature that is above the glass transition temperature of the material for a suitable period of time, and subsequently cooling the material to below the glass transition temperature. Heating can be provided through any conventional heat source and/or by exposure to one or more of ultraviolet, visible, near infrared, or infrared light.

Figures 1B, 1C:
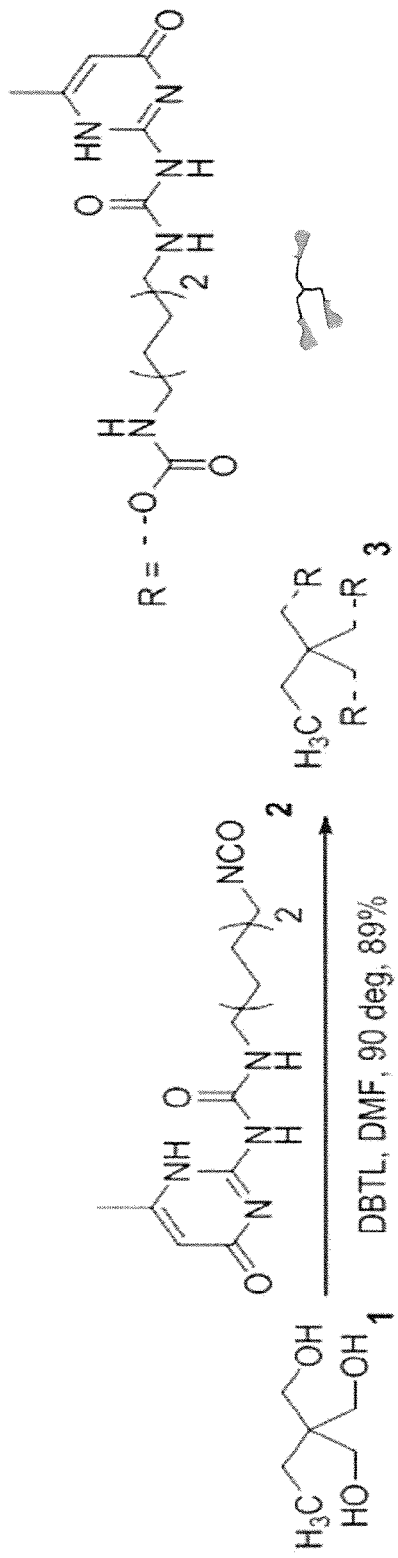

One embodiment of a stimulus-responsive supramolecular material is based on a trifunctional low-molecular weight monomer ((UPyU)$_3$TMP) that carries ureido-4-pyrimidinone (UPy) groups (FIG. 1). The UPy motif, originally developed by Meijer and coworkers, was chosen because it forms strong self-complementary hydrogen-bonded dimers, is easy to synthesize, and its dynamic binding is well investigated. However, the approach disclosed herein is general and can be adapted to other non-covalent binding motifs as noted above.

The trifunctional (UPyU)$_3$TMP introduced here was designed to form supramolecular networks, whose properties are dictated by the cross-linked nature and the large weight-fraction of the binding motif. We further surmised that the high concentration of the supramolecular motif (which causes the dynamic equilibrium to be shifted to the bound state) and the crosslinked nature (which reduces the molecular mobility of the monomers) would hamper crystallization and permit kinetic trapping of a disordered amorphous state, when the material is cooled from a dissociated melted state. Finally, we have shown recently that if used in a sufficiently high concentration, the UPy motif can serve as an efficient light-heat converter, and can be used to bestow polymers with optical responsiveness to permit features such as optical healing and (de)bonding on demand.

Figure 5:
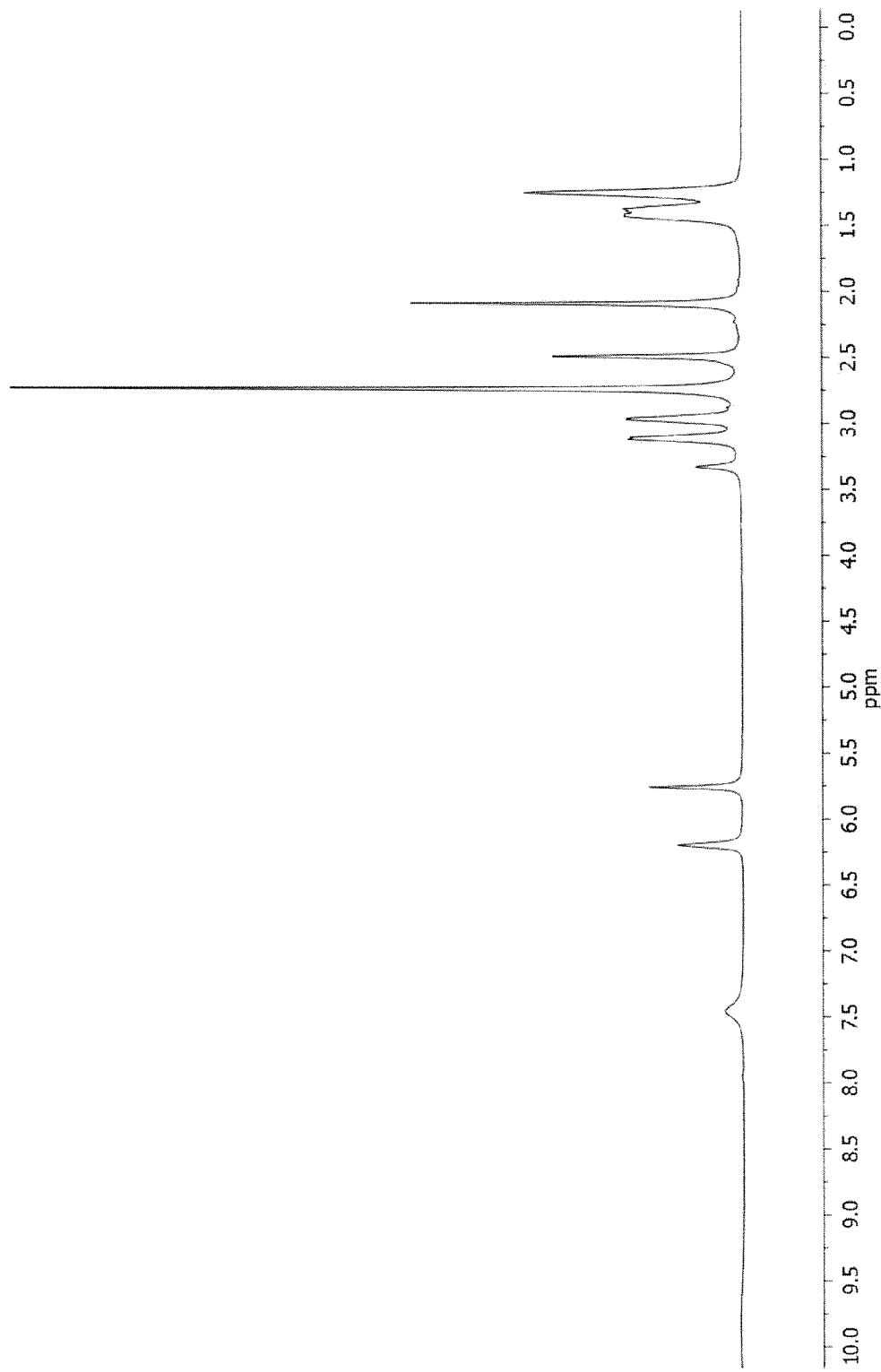
FIG. 5 illustrates $^1$H NMR spectrum of (UPyU)3TMP. $^1$H NMR (DMSO-d6, 360 MHz) δ+13.12 (s, 3H), 11.85 (s, 3H), 10.12 (s, 3H), 5.81 (s, 3H), 4.51 (s, 3H), 3.22 (t, 12H), 2.88 (s, 18H), 2.22 (s, 9H), 1.74 (s, 3H), 1.59 (t, 6H), 1.51 (t, 6H), 1.36 (s, 12H), 1.24 (s, 3H).

In a first example, (UPyU)$_3$TMP was prepared by reacting 1,1,1-tris(hydroxymethyl)propane with three equivalents of 2-(6-isocyanatohexylaminocarbonylamino)-6-methyl-4[1H] pyrimidinone using isocyanate chemistry (FIG. 1). This simple reaction, which was carried out in hot DMF to prevent network formation during the reaction, yielded the new monomer in high yield. The precipitation of the reaction mixture into cold diethyl ether afforded the product as a crystalline powder that consists of (UPyU)$_3$TMP and, quite surprisingly, three molar equivalents of DMF, as evidenced by $^1$H-NMR spectroscopy (FIG. 5).

Figure 2:
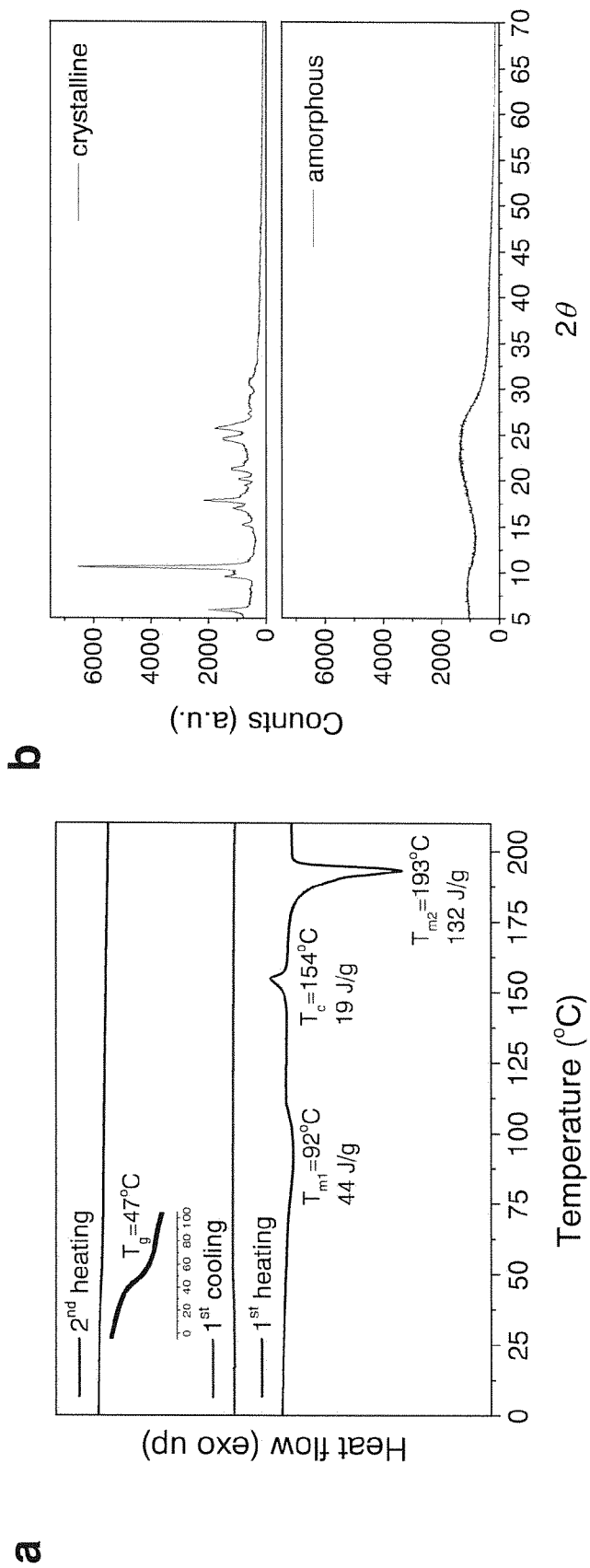
FIG. 2 represents thermal properties and morphology of (UPyU)$_3$TMP, including a) Modulated differential scanning calorimetry (DSC) traces (first heating (—), first cooling (—_ and second heating (—)) of the as-prepared material. Transition temperatures and enthalpies are indicated in the graph. The experiment was conducted with heating and cooling rates of 10° C./min under N$_2$ atmosphere, and b) Powder x-ray diffractograms for the as-prepared (top) material and a sample that had been heated to 200° C. and cooled to ambient.
Figure 6:
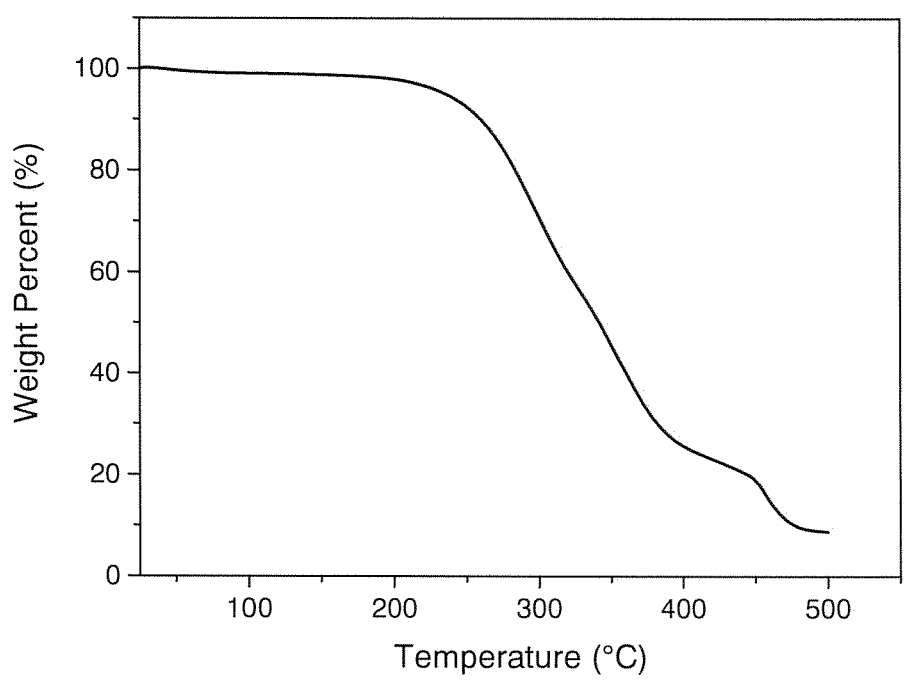
FIG. 6 illustrates the thermogravimetric analysis (TGA) curve of UPy glass from 25 to 500° C.; weight percent (—) relative to the original weight of the sample. The experiment was conducted at a heating rate of 10° C./min under N$_2$ atmosphere.
Figure 7:
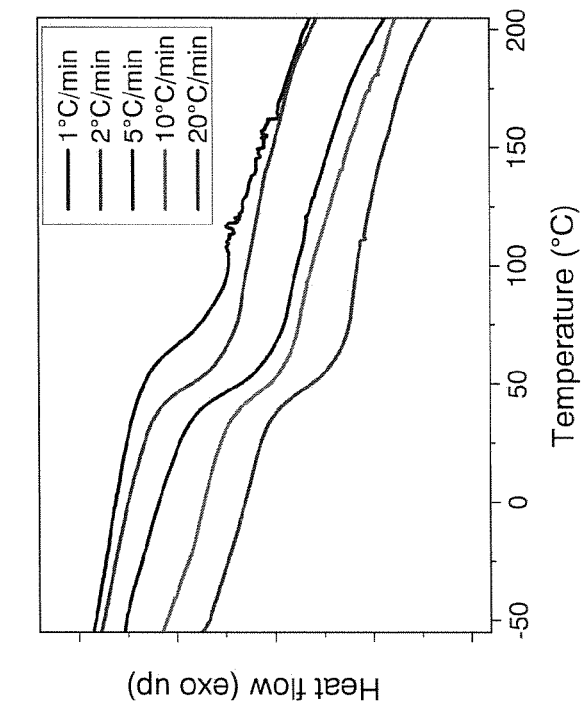
FIG. 7 illustrates DSC traces of the first cooling and second heating of (UPyU)$_3$TMP at different heating/cooling rates, a) First cooling shows a more prominent second order transition (glass transition) when higher cooling rates are used, and b) Second heating shows a shift in the glass transition temperature as a function of the heating rate. Lower heating rates result in a higher glass transition temperature.
Figure 7:
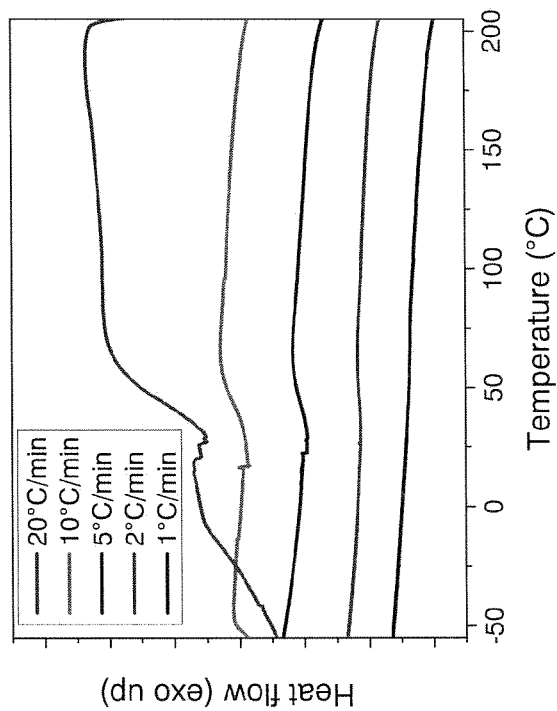

Thermogravimetric analysis (TGA) and differential scanning calorimetry (DSC) were used to determine the thermal properties of (UPyU)$_3$TMP. The TGA of the as-prepared DMF-containing (UPyU)$_3$TMP (FIG. 6) shows a 0.97% weight loss below 100° C. and only minimal additional losses up to 200° C. (total weight loss at 200° C.=2.1%); above this temperature decomposition starts to set in. The TGA data suggest that the bound DMF, which constitutes about 18 wt % of the product, does not evaporate rapidly from the crystalline sample, which melts only at 193° C. (vide infra). DSC traces of the as-prepared monomer show endothermic transitions at 92° C. (broad) and 193° C. (narrow), and a narrow exothermic transition at 154° C. (FIG. 2a). The exothermic signal around 154° C. is assigned to crystallization whereas the endotherm at 193° corresponds to melting of the crystalline powder. The cooling scan reveals a glass transition around 47° C. and is void of any other transitions, even at a cooling rate as low as 1° C. min$^{-1}$ (FIG. 6). The second DSC heating scans (FIG. 2, FIG. 7) also shows exclusively a glass transition with T$_g$=47-72° C. depending on the heating rate, demonstrating that upon melting and cooling, (UPyU)3TMP forms a largely amorphous solid. The interpretation of the DSC experiments was confirmed by powder X-ray diffraction experiments. The diffractogram of the as-prepared DMF-containing (UPyU)$_3$TMP shows well-defined reflections, while the diffractogram of a sample that had been heated to 200° C. and cooled to ambient only displays diffuse diffraction (FIG. 2b). Taken together, these data indicate that DMF-containing (UPyU)$_3$TMP does not readily crystallize after being heated to form a melt; instead, the material forms a (kinetically trapped) amorphous glass, even when cooled very slowly.

Figure 3:
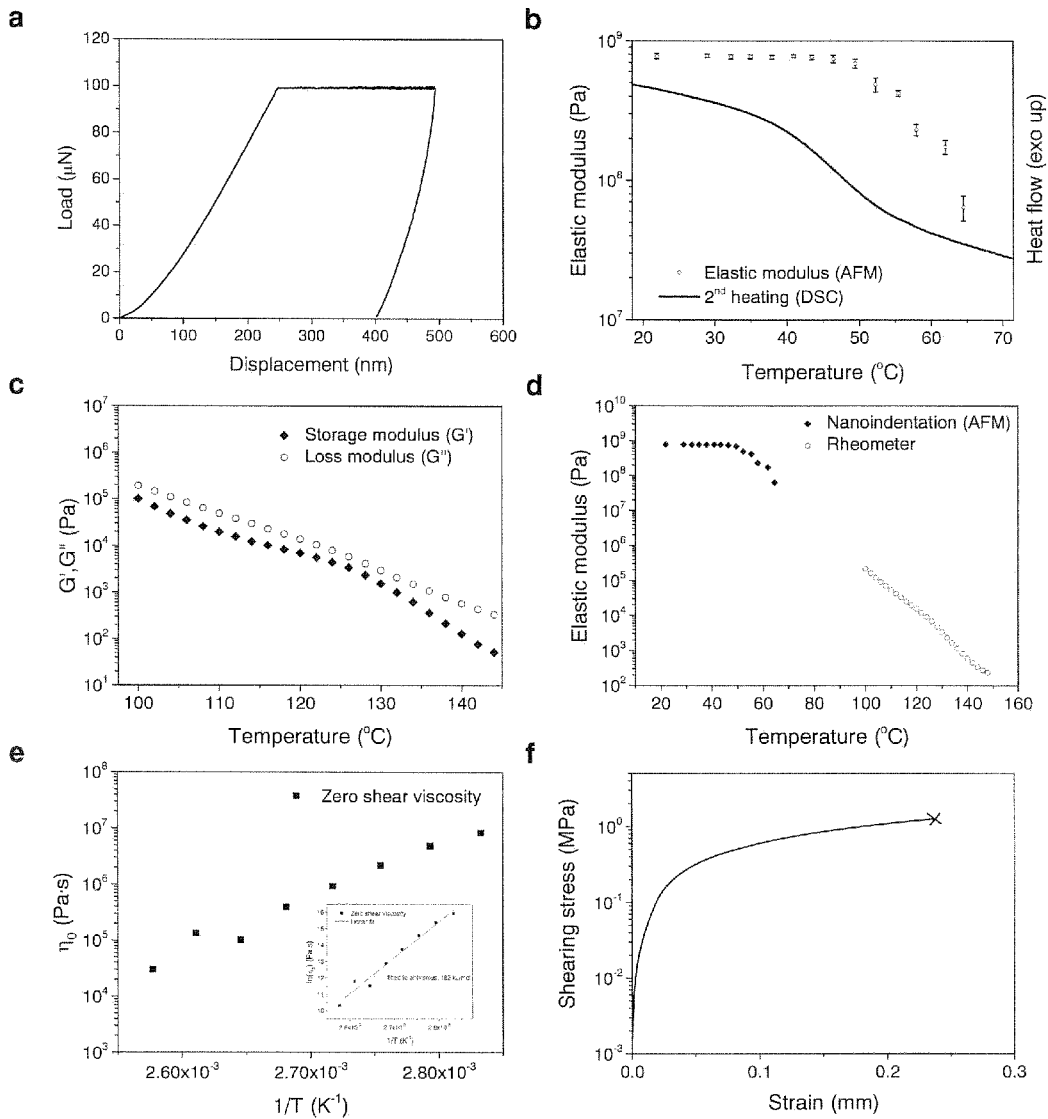
FIG. 3 illustrates mechanical and rheological properties of the (UPyU)$_3$TMP supramolecular glass, including a) Load-displacement curve acquired by depth sensing indentation. A fit of the upper 40% of the unloading curve resulted an elastic modulus of 0.96 GPa, b) Average elastic moduli (n=20) determined by AFM nanoindentation as function of temperature and heat flow determined by DSC (second heating recorded at a rate of 10 min$^{-1}$), c) Storage and loss moduli (determined at γ=0.2% and ω=20 rad/s) as function of temperature, d) Elastic moduli determined by AFM and rheological measurements as function of temperature, e) Temperature-dependence of the zero shear viscosity and a least-square fit with an Arrhenius equation, and f) Shear test of a glass lap joint bonded with (UPyU)$_3$TMP. Bonding was achieved by heating both glass slides to 200° C. with crystalline (UPyU)$_3$TMP on top. Within 60 seconds a clear viscous liquid forms, the glass slides are pressed strong together and then cooled to room temperature.
Figure 4:
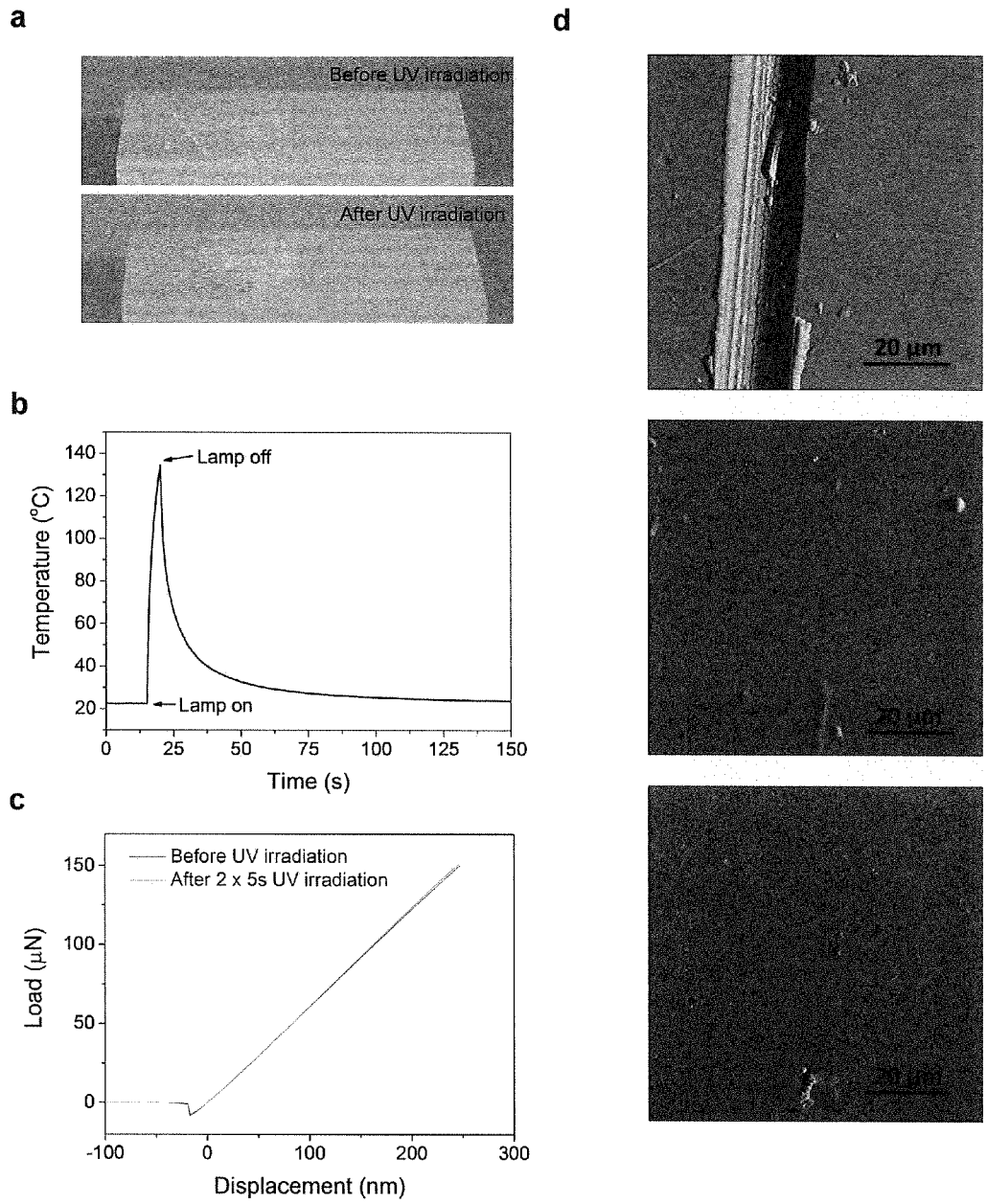
FIG. 4 illustrates optical healing of the (UPyU)$_3$TMP supramolecular glass, including a) Pictures showing the optical healing of a damaged coating on wood. The original 300 μm thin coating was cut with a razor blade (top) and subsequently exposed to the light of a UV lamp for 10 s, which caused complete healing (bottom), b) Surface temperature measure using an IR camera when a coating was irradiated with UV light for 5 s, c) Representative unloading curves of AFM nano indentation measurement of an as-prepared (—) and a healed coating (—, exposure time 2×5 s), and d) AFM images (vertical deflection) of damaged (top) and ehaled coating exposed to UV light for either 5 s (middle) or 2×5 s (bottom). In all experiments a UV light source emitting at 320-390 nm and a power density of 510 mW/cm$^2$ was used.
Figure 8:
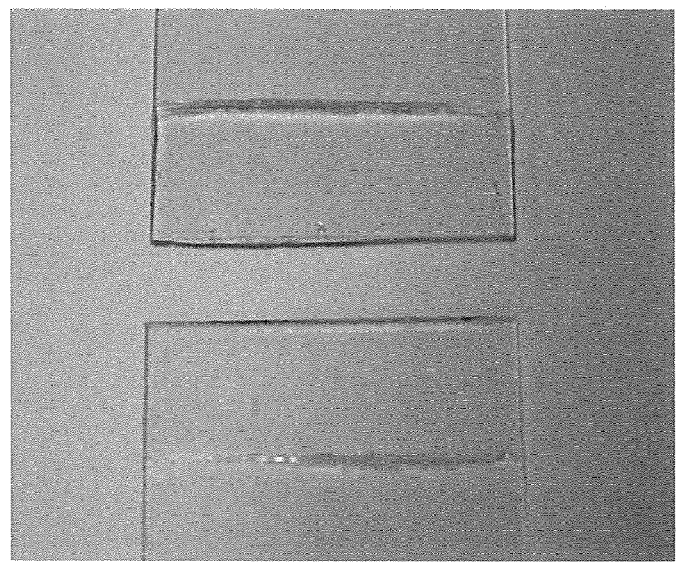
FIG. 8 illustrates an image of glass slides after failure as a result of a stress strain experiment. After failure the coating of (UPyU)$_3$TMP (around 100 μm) was only observed at one side of the glass indicating adhesive failure.
Figure 9:
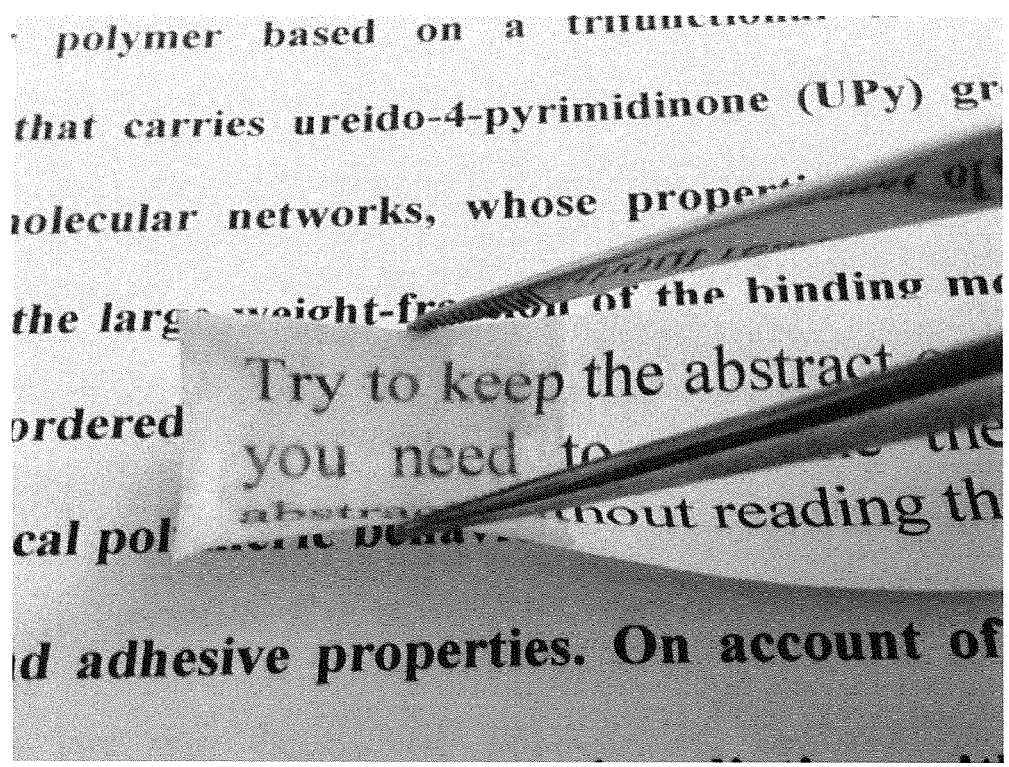
FIG. 9 illustrates an image of a piece of paper that is coated half with (UPyU)$_3$TMP. Shown is the flexibility of the coating (around 50 μm) when applied on paper.
Figure 10:
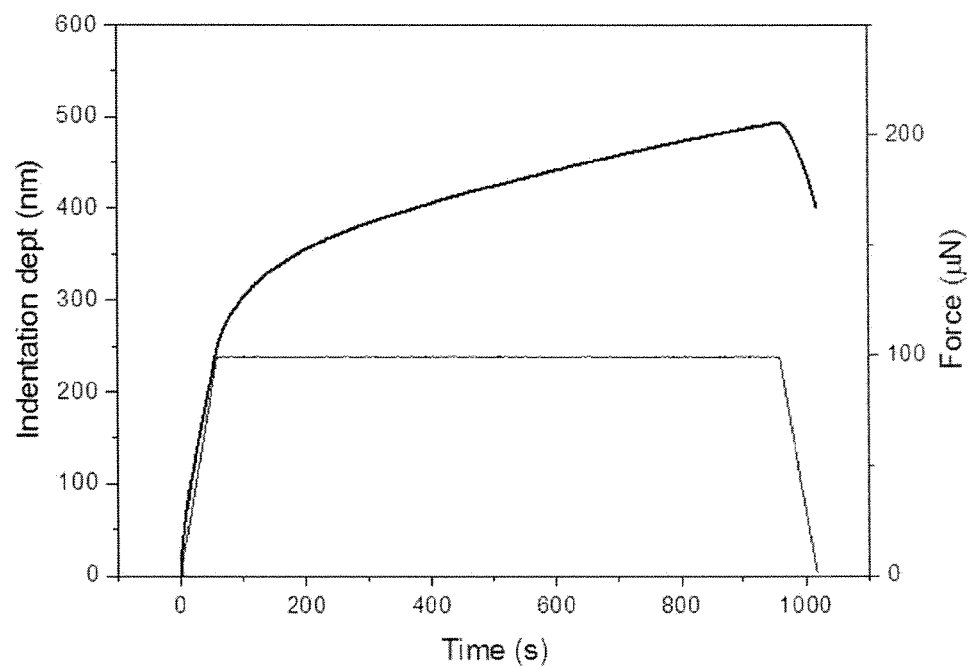
FIG. 10 illustrates a depth-sensing indentation measurement of a coating (300 μm) of (UPyU)$_3$TMP. Indentation depth (—) and force (—) are shown as function of time. A loading force of 100 μN was applied (100 μN min$^{-1}$), and kept constant for 15 minutes, than the force was unloaded (100 μN min$^{-1}$). Creep deformation was observed at constant force.
Figure 11:
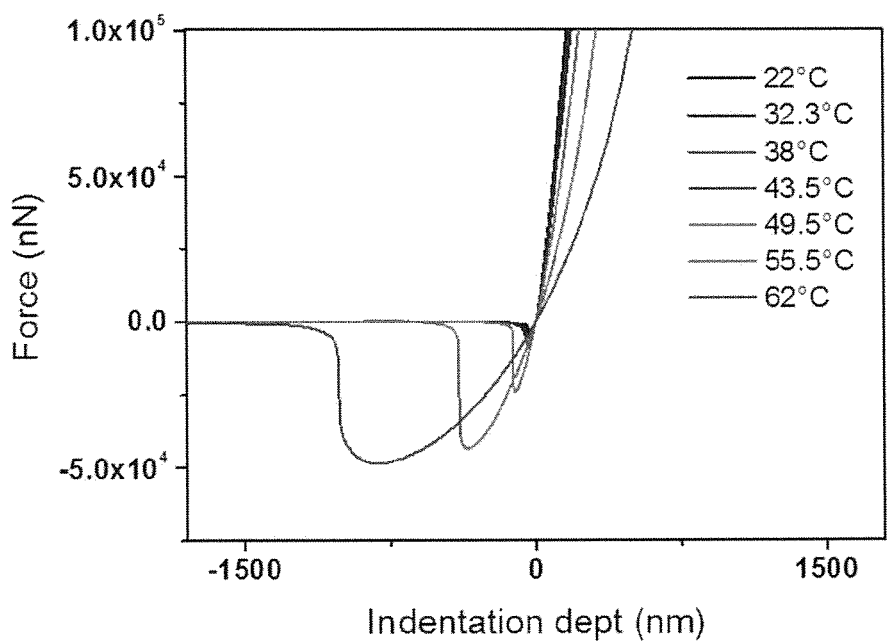
FIG. 11 illustrates AFM nanoindentation unloading curves of a coating (300 μM) of (UPyU)$_3$TMP at different temperatures. The negative forces that were measured during unloading indicate adhesion. More adhesion was observed with increasing temperature.
Figure 12:
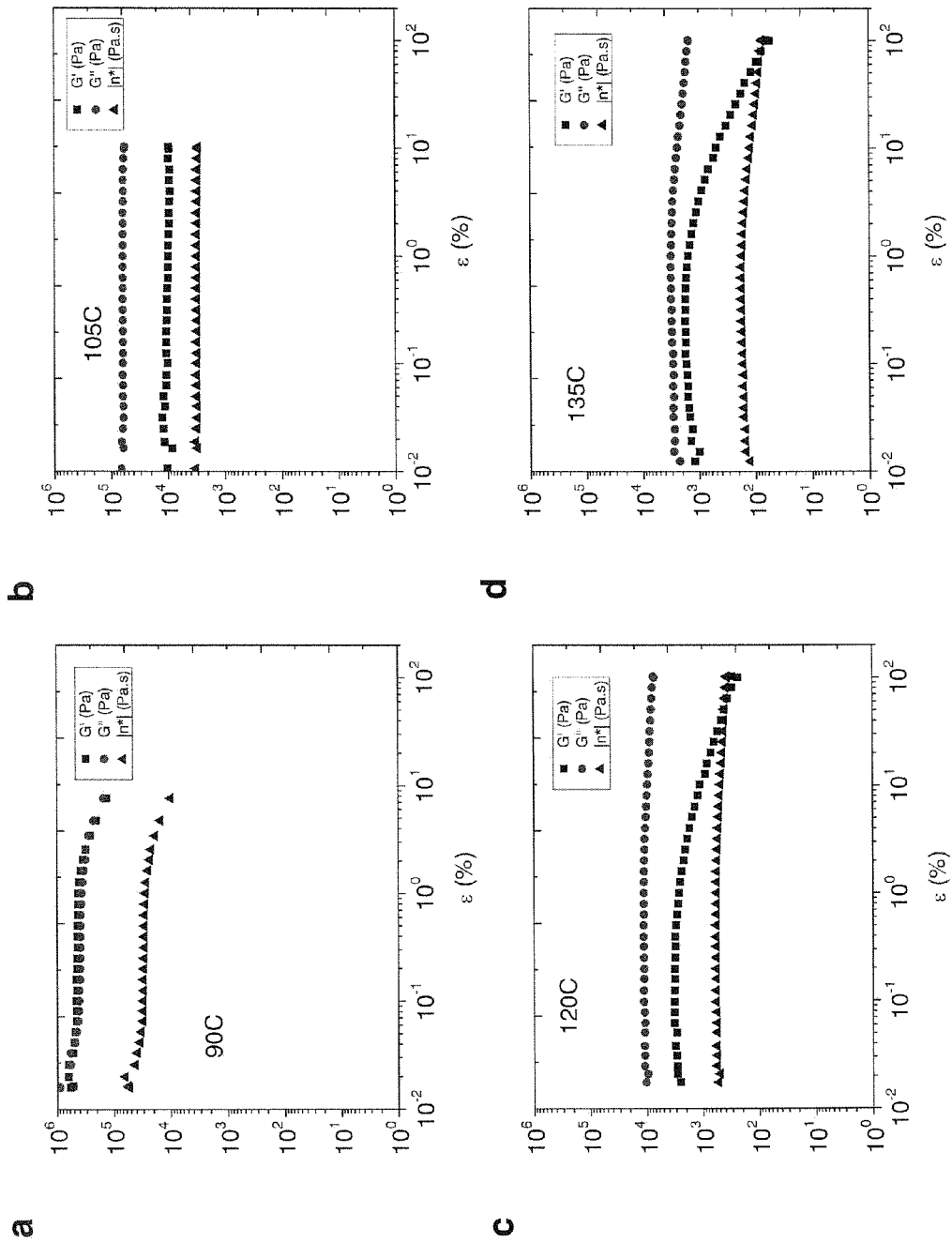
FIG. 12 illustrates strain sweep curves acquired by rheological studies of (UPyU)$_3$TMP at: a. 90° C., b. 105° C., c. 120° C., d. 135° C.
Figure 13:
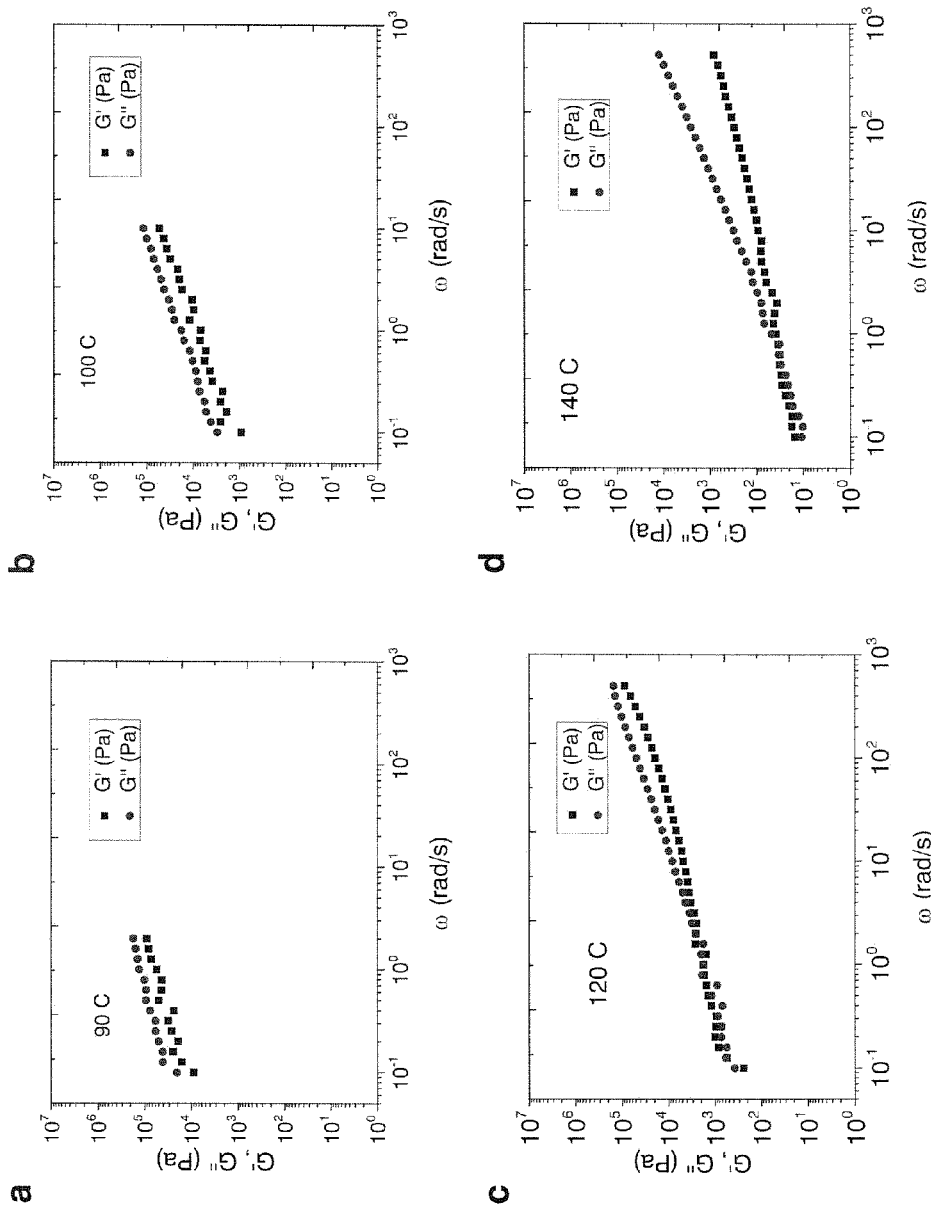
FIG. 13 illustrates frequency sweep curves acquired by rheological studies of (UPyU)$_3$TMP at: a. 90° C., b. 100° C., c. 120° C., d. 140° C.

DMF-containing (UPyU)$_3$TMP can readily be melt-processed into solid supramolecular objects of various shapes by heating either the as-prepared crystalline monomer or material that had previously been converted into a glassy form to 200° C. (i.e., above the Tm) to form of a clear, slightly viscous liquid. Glassy samples could also be processed at lower temperature, but the viscosity increased as the temperature was decreased (vide infra). Subsequent cooling to room temperature, optionally in a mold, afforded a transparent hard material, for example in the form of self-standing films (FIG. 1c) or coatings on substrates such as wood, glass, or paper (FIGS. 4, 8, 9). While thin coatings on paper were found to remain intact upon flexing the substrate, free-standing films were rather brittle and prevented characterization of the material's mechanical properties by tensile testing or dynamic mechanical analysis. Therefore, a ca. 300 µm thin (UPyU)$_3$TMP supramolecular glass film was applied onto a glass substrate, and the mechanical properties were investigated by depth-sensing indentation and temperature-dependent atomic force microscopy (AFM) experiments using a force spectroscopy mode. Depth-sensing indentation revealed a Young's modulus of 0.96 GPa at ambient temperature (FIG. 3a). These experiments were conducted using the widely used procedure by Oliver and Pharr (Oliver, W. C. & Pharr, G. M. Measurement of hardness and elastic modulus by instrumented indentation: Advances in understanding and refinements to methodology. J. Mater. Res. 19, 3-20, (2004)). In spite of the glassy nature at this temperature, significant creep was observed when a constant load was applied for an extended period of time, revealing a viscoelastic character of the amorphous material (FIG. 10). Gratifyingly, AFM force spectroscopy measurements revealed a comparable Young's modulus (0.78±0.04 GPa) at room temperature (FIG. 3b). They also showed a significant modulus decrease upon heating, with an onset around 46° C. A comparison with the DSC data reveals that this stiffness decrease is associated with the transition from the glassy into a rubbery state. AFM force spectroscopy measurements also reveal a significant increase in adhesion above Tg (FIG. 11). The AFM data permit the conclusion that the UPy-UPy interactions are not simply "switched off" when the (UPyU)$_3$TMP supramolecular glass is heated above T$_g$; instead, a dynamic equilibrium between bound and dissociated states exists, which is shifted to the monomer side as the temperature is increased. To confirm this situation, which is consistent with previous studies on the UPy dimerization as a function of temperature, rheological studies were conducted. Strain sweep experiments performed in the linear viscoelastic regime (FIG. 12) show a frequency dependence of the storage and loss modulus between 90° C. and 140° C. (FIG. 13), suggesting polymer-like viscoelastic properties. Further, a significant decrease of the storage and loss modulus was observed upon heating the material (FIG. 3c), suggesting a drop of the virtual molecular weight on account of reducing the cross-link density by shifting the dynamic equilibrium towards the dissociated state. We note that when DMF-containing (UPyU)$_3$TMP was kept in the rheometer at 150° C. for an hour, an increase of the viscosity was observed; as this effect could be erased upon heating the sample to 180° C. and subsequent cooling, we interpret this with partial crystallization of the super-cooled melt. The extrapolation of the rheology data to lower temperatures (FIG. 3d) reveals that the two experimental techniques used to determine the elastic modulus paint a consistent picture regarding the temperature-dependence of the new material. Plotting the zero shear viscosity η* as a function of the reciprocal temperature (1/T) (FIG. 3e) and fitting the data to an Arrhenius equation of the form:

$$\eta^* =_A e^{\Delta H/RT} \qquad \text{Eq.1}$$

resulted an activation enthalpy ΔH for stress relaxation of 182 kJ mol$^{-1}$, which is about 50% higher than the ΔH reported for telechelic tri-dimethylsiloxane terminated with two UPy motifs, see Ky Hirschberg, J. H. K.; Beijer, F. H.; van Aert, H. A.; Magusin, P. C. M. M.; Sijbesma, R. P.; Meijer, E. W., Macromolecules, 1999, 32, pp. 2696-2705, and consistent with the higher number of UPy groups in (UPyU)3TMP.

The targeted optically responsive nature of the new supramolecular glass relies on the conversion of (locally harnessed) optical energy into heat by nonradiative relaxation, which causes reversible dissociation of the supramolecular motifs and temporarily liquefies the material. We first tested this by using (UPyU)3TMP as a reversible supramolecular adhesive. Single lap joints were prepared by joining two glass substrates that had each been coated with a 300 µm thin film of the glassy material, bonding them by heating to 200° C. for 60 sec, and cooling to ambient (FIG. 8). The lap joints displayed a shear stress of 1.2±0.1 MPa (FIG. 3f), which is comparable to that of other supramolecular adhesives that have been previously reported, see Heinzmann, C.; Coulibaly, S.; Roulin, A.; Fiore, G. L.; Weder, C. ACS Appl Mater Interfaces 2014, 6, 4713.

Figure 14:
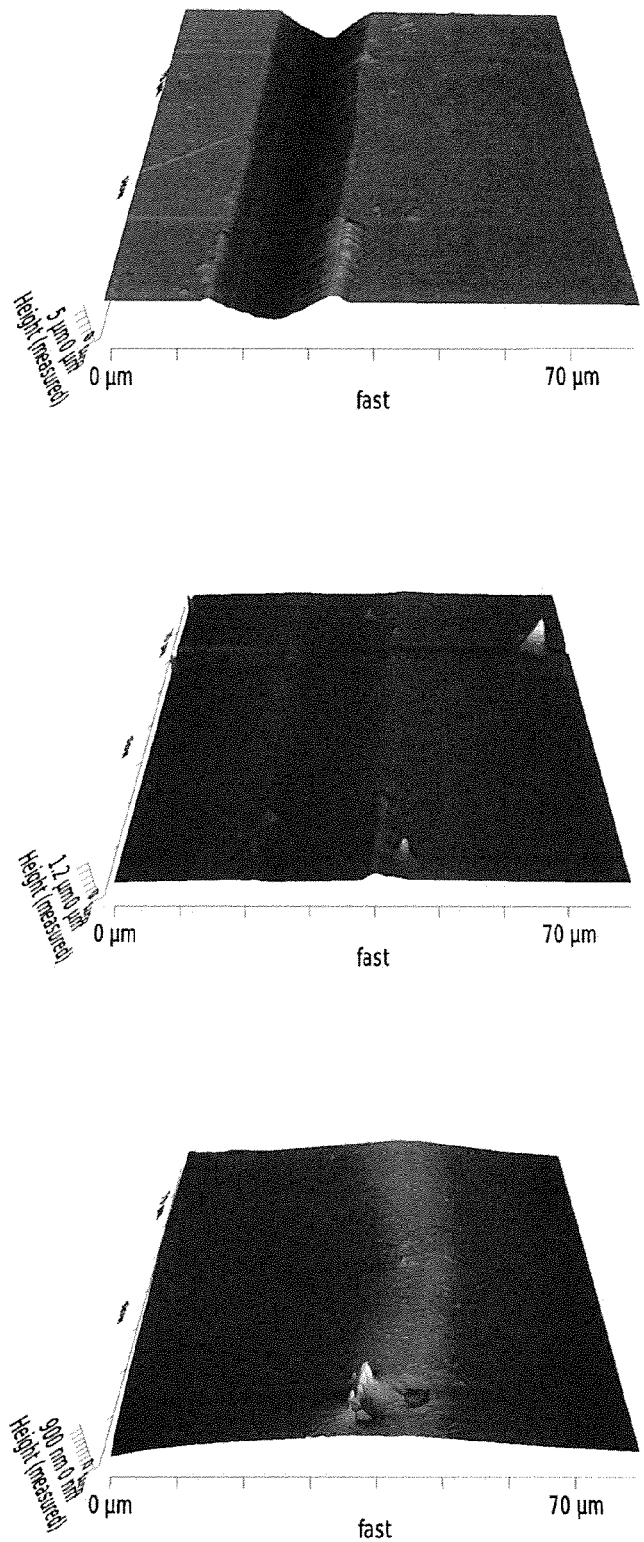
FIG. 14 illustrates three dimensional AFM height images. A cut was made in a coating (300 μm) of (UPyU)$_3$TMP with a razor blade. UV irradiation (320-390 nm, 500 mW cm$^{-1}$) was applied (5 s) two times. AFM images are shown of damaged (top), after 5 s of UV irradiation (middle), and after 2 times 5 sec UV irradiation (bottom).

The large optical absorption imparted by the high UPy content, and the capability to dissociate into a low-viscosity melt should bestow the supramolecular (UPyU)$_3$TMP glass with excellent optical healing capabilities. To test this, a piece of wood was coated with a 300 μm thin layer of amorphous (UPyU)$_3$TMP and the coating was intentionally damaged by cutting with a razor blade (FIG. 4a). The damaged area was subsequently exposed to UV irradiation (320-390 nm, 510 mW/cm$^2$) for 10 s, which led to complete disappearance of the cut (FIG. 4a). We subsequently reduced the healing time to 5 s and monitored the temperature increase of the material with the help of an infrared thermometer; the data show a rapid and localized temperature increase to 135° C. (FIG. 4b) and again, the cut completely disappeared. AFM images (FIG. 4d) show that a ca. 20 μm wide cut is completely filled after 5 s of UV exposure, and a consecutive 5 s exposure resulted in the complete removal of the scratch, although a very shallow scar remained (FIGS. 4d, 14). We employed AFM nanoindentation measurements to determine the mechanical properties of the supramolecular (UPyU)$_3$TMP glass in the pristine film, and after cutting and healing. Gratifyingly, the load displacement curves of the original and the healed material are identical, indicating quantitative restoration of the original mechanical properties (FIG. 4c).

Figure 15:
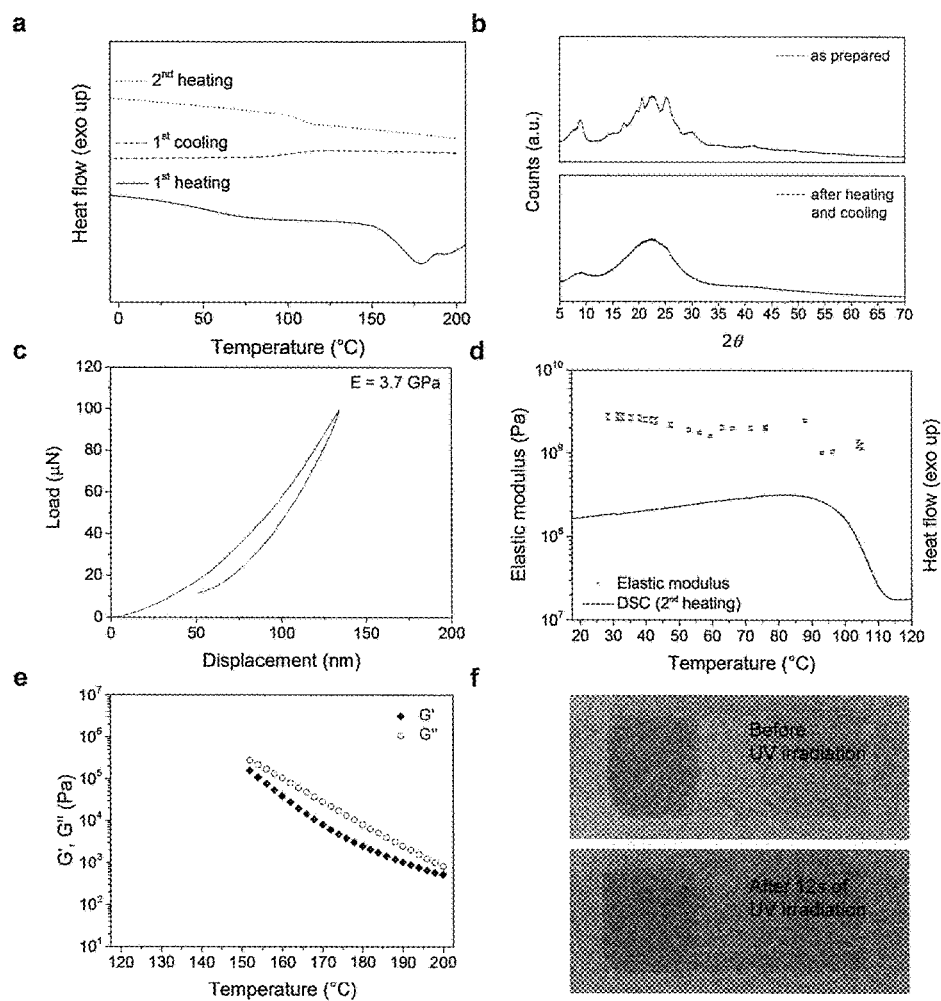
FIG. 15 illustrates material properties of DMF-free (UPyU)3TMP. DMF-free (UPyU)$_3$TMP was prepared in pyridine to prevent coordination of solvent. a. Differential scanning calorimetry (DSC) traces (first heating (—), first cooling ( - - - ) and second heating ( . . . )) of the as-prepared material. Transition temperatures and enthalpies are indicated in the graph. The experiment was conducted with heating and cooling rates of 10° C.·min$^{-1}$ under N2 atmosphere. b. Powder X-ray diffractograms for the as-prepared (top) material and a sample that had been heated to 200° C. and cooled to ambient. c. Load-displacement curve acquired by depth sensing indentation. A fit of the unloading curve resulted an elastic modulus of 3.7 GPa. d. Average elastic moduli (n=20) determined by AFM nanoindentation as a function of temperature; also shown is the heat flow determined by DSC (second heating recorded at a rate of 10° C.·min$^{-1}$). e. Storage (G') and loss (G") moduli (determined at γ=0.2% and ω=20 rad·s$^{-1}$) as function of temperature. f. Pictures showing the optical healing of a damaged coating on wood. The 300 μm thin coating was cut with a razor blade (top) and subsequently exposed to UV light for 12 s, which caused complete healing (bottom).

In a second set of experiments, the material properties of DMF-free (UPyU)$_3$TMP were studied. To that end (UPyU)$_3$TMP was prepared in hot pyridine instead of DMF, and (UPyU)$_3$TMP was obtained without a co-crystallized solvent. DSC studies revealed that the as-prepared DMF-free material also exhibits some crystallinity (FIG. 15a). Also in this case, the cooling scan, acquired after first heating the material to the melted state, reveals only a glass transition and is, as the subsequent heating scan, void of any other transitions. The fact that the T$_g$ of 106° C. of the DMF-free (UPyU)$_3$TMP is higher than that of the DMF-containing (UPyU)$_3$TMP shows that the DMF has a plasticizing effect. The interpretation of the DSC experiments was confirmed by powder X-ray diffraction experiments. The diffractogram of the as-prepared DMF-free (UPyU)$_3$TMP shows well-defined reflections, while the diffractogram of a sample that had been heated to 200° C. and cooled to ambient only displays diffuse diffraction, indicative of the substantially amorphous nature of the material (FIG. 15b). Depth sensing indentation experiments (FIG. 15c) showed virtually no creep deformation and revealed an elastic modulus of 3.7 GPa, which is much higher than that of the DMF-containing material of 0.96 GPa. Temperature dependent AFM force spectroscopy measurements showed the elastic modulus to be constant as function of temperature up to T$_g$ (FIG. 15d). The rheology of the DMF-free material shows a similar trend as function of temperature shifted to higher temperatures (FIG. 15e) confirming that in the DMF-containing material the solvent is acting as competitive hydrogen bond acceptor that is reducing the crosslinking density and therefore resulting in a shift of the temperature dependent rheology to lower temperatures. Optical healing of the DMF-free material was also possible (FIG. 15f) although a longer exposure time was necessary to achieve healing than in the case of the DMF-containing sample.

In summary, we have developed novel stimulus-responsive glass-forming supramolecular material which, in spite of the low-molecular weight nature of the building block, displays typical polymeric behavior, including high stiffness in the glassy state, viscoelastic behavior in the melt, and excellent coating and adhesive properties. Two specific characteristics appear to be particularly important in the context of the development of healable coatings. To our best knowledge the supramolecular (UPyU)$_3$TMP glass is not only stiffer than any other optically healable polymer reported to date, but the material also heals much faster. This attractive combination of properties is a direct result of the design principle applied, i.e., the use of a low-molecular weight multifunctional building block to form a dynamic, disordered supramolecular network, which can readily be frozen into a glassy solid. The concept is broadly applicable to other supramolecular glasses comprised of multifunctional monomer with binding motifs that exhibit sufficiently dynamic supramolecular interactions and can promote light and/or heat conversion. The materials of the present invention can be supplemented with components utilized to toughen conventional thermosetting polymers. For example, in one embodiment, 10 wt % of UPy functionalized cellulose nanocrystals (CNC) was mixed with (UPyU)$_3$TMP at 200° C. for 5 min, resulting in a clear viscous liquid. Cooling the material, and subsequent compression molding at 140° C. resulted in a qualitatively stiffer, less brittle easier processable material than the neat (UPyU)$_3$TMP.

Materials.

All reagents were used as received. 2(6isocyanatohexylaminocarbonylamino)-6-methyl-4[1H]pyrimidinone (UPy isocyanate synthon) was synthesized as previously reported, see Folmer, B. J. B.; Sijbesma, R. P.; Versteegen, R. M.; van der Rijt, J. A. J.; Meijer, E. W. Adv. Mater. 2000, 12, 874.

Methods.

$^1$H (360 MHz) and $^{13}$C (90 MHz) NMR spectra were recorded on a Bruker Advance III spectrometer in DMSO-d6. $^1$H NMR coupling constants are given in Hz. $^1$H NMR spectra were referenced against the signal for residual DMSO at 2.50 ppm and $^{13}$C NMR spectra were referenced against the DMSO-d6 signal at 39.52 ppm. Thermogravimetric analyses (TGA) were conducted under N$_2$ using a Mettler-Toledo STAR thermogravimetric analyzer in the range of 25° C. to 500° C. with a heating rate of 10° C./min. Differential scanning calorimetry (DSC) measurements were performed under N$_2$ using a Mettler-Toledo STAR system modulated differential scanning calorimeter operated in modulated mode (amplitude ±1° C., period 60 s, heating/cooling rate 10° C./min, range −70 to 150° C.). Data from the second heating cycle and the reverse heat flow curve are reported unless indicated otherwise (T$_d$=onset point of decomposition, T$_g$=glass transition temperature).

Synthesis of UPy Functionalized DMF-Containing 1,1,1-tris(hydroxymethyl)propane ((UPyU)$_3$TMP)

A round bottom flask was charged with 1,1,1-Tris(hydroxymethyl)propane (1.45 g, 10.8 mmol), UPy isocyanate synthon (14.25 g, 48.6 mmol), dibutyltin dilaurate (5 drops) and dry DMF (750 mL) under an N$_2$ atmosphere. The reaction mixture was heated up to 90° C. and stirred for 48 h. The progress of the reaction was followed by FT-IR, and after 48 h there was no further decrease in the isocyanate peak at 2269 cm$^{-1}$ observed. Aminopropyl functionalized silica (25 g) was added to eliminate excess UPy isocyanate synthon and stirred for 1 h. The reaction mixture was cooled down to room temperature, and all solids were removed by vacuum filtration. The filtrate was concentrated in vacuo to 250 mL, and was precipitated in ice cold diethyl ether (800 mL). The precipitate was collected by vacuum filtration and dried in vacuo at 70° C. for 24 h to afford the product as white crystalline powder (11.90 g, 9.65 mmol, 89%). Yield based on the molecular weight plus the coordination of three molecular equivalents of DMF as evidenced by $^1$H-NMR. $^1$H NMR (DMSO-d6, 360 MHz) δ=13.12 (s, 3H), 11.85 (s, 3H), 10.12 (s, 3H), 5.81 (s, 3H), 4.51 (s, 3H), 3.22 (t, 12H), 2.88 (s, 18H), 2.22 (s, 9H), 1.74 (s, 3H), 1.59 (t, 6H), 1.51 (t, 6H), 1.36 (s, 12H), 1.24 (s, 3H). Signal at δ=2.88 belonging to (3 molecular equivalents of) DMF. $^{13}$C NMR (DMSO-d6, 91 MHz,) δ=173.67, 158.98, 156.99, 155.13, 148.73, 147.08, 107.05, 103.68, 41.11, 40.10, 36.59, 30.56, 29.85, 26.75, 19.35. ESI-MS: m/z: calcd: 1014.1. found: 1037.4 [M+Na]$^+$ Synthesis of DMF-Free UPy Functionalized 1,1,1-Tris(Hydroxymethyl)Propane ((UPyU)$_3$TMP)

A round bottom flask equipped with a reflux cooler was charged with 1,1,1-tris(hydroxymethyl)propane (635 mg, 4.7 mmol), UPy isocyanate (5.0 g, 17 mmol), dibutyltin dilaurate (300 μL, ~3 mol %) and dry pyridine (300 mL) under an N$_2$ atmosphere. The reaction mixture was heated to reflux temperature (120° C.) and was stirred for 36 h under reflux. Aminopropyl functionalized silica (5 g) was added to eliminate any excess of the UPy isocyanate. The reaction mixture was stirred for an additional 30 min at reflux temperature to prevent precipitation of the product. The reaction mixture was cooled to 100° C. and solids were removed from the reaction mixture by vacuum filtration. The filtrate was cooled to room temperature and a white precipitate was observed. Acetone (200 mL) was added to the filtrate, and the solids were collected by filtration. The precipitate was washed with acetone (3×100 mL) and dried in vacuo at 70° C. for 12 h to yield the analytically pure product as white crystalline powder (3.7 g, 3.6 mmol, 53%). We note that the product has poor solubility in common solvents, therefore all NMR samples were prepared by heating to 100° C. in DMSO-d6 for 20 min to achieve complete dissolution (c=2 mg/mL). Cooling to room temperature resulted in solution that were stable for up to 2 h. $^1$H NMR (DMSO-d6, 360 MHz) δ=11.53 (s, 3H), 9.67 (s, 3H), 7.39 (s, 3H), 7.09 (s, 3H), 5.76 (s, 3H), 3.85 (ds, 6H), 3.12 (t, 6H), 2.93 (s, 6H), 2.10 (s, 9H), 1.43-1.27 (bm, 26H), 0.8 (s, 3H). $^{13}$C NMR (DMSO-d6, 91 MHz) δ=173.67, 158.98, 156.99, 155.13, 148.73, 147.08, 107.05, 103.68, 41.11, 40.10, 36.59, 30.56, 29.85, 26.75, 19.35. ESI-MS: m/z: calcd: 1014.1. found: 1014.2. Anal. Calcd for C45H71N15O12: C, 53.29; H, 7.06; N, 20.72. Found: C, 53.30; H, 7.46; N, 20.80.

Indentation Measurements.

For indentation measurements, a glassy (UPyU)$_3$TMP coating with a thickness of around 300 μm was prepared by melt deposition at 200° C. onto a thin glass substrate. The coating thickness was chosen with respect to Buckle's one-tenth law to avoid any influence of the substrates on the measurement (Westbrook, J. H. J. H., Conrad, H. & Metals, A. S. f. *The Science of hardness testing and its research applications* (American Society for Metals, 1973)), and maximum indentation depths did not exceed 3 μm (less than 1%).

Atomic force microscopy (AFM) images and force spectroscopy measurements were performed on a JPK Nano Wizard II. AFM images were recorded with NanoWorld NCHR high resonance frequency tips. Force spectroscopy tests were performed with a Bruker DNISP cantilever with a cube corner diamond tip (nominal sensitivity=249 N m$^{-1}$).

Temperature-dependent AFM force spectroscopy tests were performed on coatings with a thickness of around 300 μm on a thin round microscopy glass slide and placed on a JPK HTHS high temperature heating stage, and the sample surface temperature was monitored using a hand-held IR camera. An indentation force of 150 μN was chosen to respect the indentation depth limitation dictated by Buckle's Law regarding effects of the substrate. All recorded unloading curves were fitted (upper 50% of the unloading curve) and analyzed according to the Oliver & Pharr model to yield the elastic modulus, assuming a Poisson ratio of 0.3, and a perfect cube corner tip (Oliver, W. C. & Pharr, G. M. Measurement of hardness and elastic modulus by instrumented indentation: Advances in understanding and refinements to methodology. *J. Mater. Res.* 19, 3-20, (2004)).

As a control experiment to improve the reliability of the fitted data, AFM images of indents (for indentation forces of 150 μN and 300 μN) were acquired. Perfect cube corner indents with only limited pile-up were seen, especially for indents with a force of 150 μN, which was used for all AFM force spectroscopy experiments.

Load-sensing indentation measurements were performed using a CSM Ultra Nanoindenter equipped with a Berkovich tip (diamond). The experiments were performed using a loading and unloading rate of 100 μN min$^{-1}$, and 15 min of constant load (100 μN) before unloading to allow for creep deformation. Prior to each measurement a height calibration of the local sample surface was performed. Unloading curves were used to determine the elastic modulus according to the Oliver & Pharr model using CSM nanoindentation software (Oliver, W. C. & Pharr, G. M. Measurement of hardness and elastic modulus by instrumented indentation: Advances in understanding and refinements to methodology. *J. Mater. Res.* 19, 3-20, (2004)).

While in accordance with the patent statutes the best mode and preferred embodiment have been set forth, the scope of the invention is not limited thereto, but rather by the scope of the attached claims.

What is claimed is:

1. A stimulus-responsive supramolecular material, comprising:
   monomers having three or more identical or different binding sites that permit non-covalent, directional interactions between multiple monomer molecules, wherein monomers comprising urido-4-pyrimidinone groups are utilized, wherein the at least one monomer has a molar mass of at least 1000 g/mol, wherein
   in a first un-switched state the material is in a substantially disordered glassy state with multiple monomer molecules being crosslinked and is characterized by an elastic modulus of at least 500 MPa, and wherein
   in a second switched state, the material is in a fluid state, wherein
   switching between the first un-switched state and the second switched state is inducible by an optical stimulus or thermal stimulus or a combination thereof, and
   wherein at least at one temperature viscoelastic behavior is observed, and
   wherein said substantially disordered glassy state and said viscoelastic behavior are achieved by said at least one monomer having binding sites that are at least partially associated at least at one temperature that is higher than the glass transition temperature.

2. The stimulus-responsive supramolecular material according to claim 1, wherein the stimulus is light.

3. The stimulus-responsive supramolecular material according to claim 2, wherein the monomers consist of only one monomer type.

4. The stimulus-responsive supramolecular material according to claim 3, wherein all binding sites are identical.

5. The stimulus-responsive supramolecular material according to claim 1, wherein in the first un-switched state the material is characterized by an elastic modulus of more than 2 GPa.

6. The stimulus-responsive supramolecular material according to claim 1, wherein in a second switched state, the material is a Newtonian fluid.

7. The stimulus-responsive supramolecular material according to claim 1, wherein in a second switched state, the material is a non-Newtonian fluid.

8. The stimulus-responsive supramolecular material according to claim 1, wherein in the first un-switched state the material is characterized by a glass transition temperature of at least 40° C.

9. The stimulus-responsive supramolecular material according to claim 1, wherein damage to the material can be repaired upon exposure to light.

10. The stimulus-responsive supramolecular material according to claim 1, wherein the material additionally comprises at least one nanofiller.

11. The stimulus-responsive supramolecular material according to claim 1, wherein the binding sites include one or more of a motif capable of forming hydrogen bonds, metal-ligand complexes, charge-transfer complexes, or ion pairs.

12. A method for healing a damaged portion of stimulus-responsive supramolecular material according to claim 1, comprising the steps of: heating the damaged portion to a temperature that is above a glass transition temperature of the material for a period of time, and subsequently cooling the material to below the glass transition temperature.

13. The method according to claim 12, wherein the material is heated through exposure to ultraviolet, visible, near infrared or infrared light or a combination thereof.

14. A composite, comprising a stimulus-responsive supramolecular material according to claim 1 located on a substrate.

15. The method according to claim 12, wherein one or more of the follow conditions apply to the stimulus-responsive supramolecular material: wherein the stimulus is light; wherein the at least one monomer consists of only one monomer type; wherein all binding sites are identical; wherein in a second switched state, the material is a Newtonian fluid; wherein in a second switched state, the material is a non-Newtonian fluid; wherein the at least one monomer has a molar mass of at least 1000 g/mol; wherein in the first un-switched state the material is characterized by a glass transition temperature of at least 40° C.; wherein damage to the material can be repaired upon exposure to light; wherein the material additionally comprises at least one nanofiller; and wherein the material comprises $(UPyU)_3TMP$.

16. A stimulus-responsive supramolecular material, comprising:
at least one monomer having three or more identical or different binding sites that permit non-covalent, directional interactions between multiple monomer molecules, wherein the monomer comprises $(UPyU)_3TMP$, wherein
in a first un-switched state the material is in a crosslinked, substantially disordered glassy state and is characterized by an elastic modulus of at least 500 MPa, and wherein
in a second switched state, the material is in a fluid state, wherein
switching between the first un-switched state and the second switched state is inducible by an optical stimulus or thermal stimulus or a combination thereof, and
wherein at least at one temperature viscoelastic behavior is observed, and
wherein said substantially disordered glassy state and said viscoelastic behavior are achieved by said at least one monomer having binding sites that are at least partially associated at least at one temperature that is higher than the glass transition temperature.

17. The stimulus-responsive supramolecular material according to claim 1, wherein the monomer has a high weight fraction of the motif including the binding site.

* * * * *